United States Patent [19]

Baudier et al.

[11] Patent Number: 4,859,469
[45] Date of Patent: Aug. 22, 1989

[54] NOVEL GALENIC FORMS OF VERAPAMIL, THEIR PREPARATION AND MEDICINES CONTAINING SAID NOVEL GALENIC FORMS

[75] Inventors: Philippe Baudier, Waterloo; Arthur De Boeck, Herne; Jacques Fossion, Braine-L'Alleud, all of Belgium

[73] Assignee: Pharlyse Societe Anonyme, L-Luxembourg Ville, Luxembourg

[21] Appl. No.: 909,054

[22] Filed: Sep. 18, 1986

[30] Foreign Application Priority Data

Sep. 18, 1985 [LU] Luxembourg ............................ 86077

[51] Int. Cl.⁴ ................................................ A61K 9/58
[52] U.S. Cl. ..................... 424/462; 424/457; 424/458; 424/459; 424/461; 424/493; 424/494; 424/495; 424/497
[58] Field of Search ............... 424/493, 494, 495, 497, 424/462, 461, 459, 458, 457

[56] References Cited

U.S. PATENT DOCUMENTS

| | | | |
|---|---|---|---|
| 4,411,882 | 10/1983 | Franz et al. | 424/462 |
| 4,521,401 | 6/1985 | Dunn | 424/480 |
| 4,629,624 | 12/1986 | Grouiller et al. | 514/951 X |
| 4,656,024 | 4/1987 | Laruelle | 424/497 |

Primary Examiner—Thurman K. Page
Attorney, Agent, or Firm—Sughrue, Mion, Zinn, Macpeak & Seas

[57] ABSTRACT

The invention relates to a novel galenic form of verapamil which show an excellent bioavailability. The novel galenic form comprises microgranules containing a verapamil addition salt with an acid, associated to at least one wetting agent. The microgranules are coated with a porous membrane constituted of a synthetic polymer associated to an adjuvant.

17 Claims, 5 Drawing Sheets

NOVEL GALENIC FORMS OF VERAPAMIL, THEIR PREPARATION AND MEDICINES CONTAINING SAID NOVEL GALENIC FORMS

BACKGROUND OF THE INVENTION

The present invention relates to novel galenic forms of verapamil, their manufacture and medicines containing said novel galenic forms.

Verapamil or 5-(3,4-dimethoxyphenylethyl)methyl-2-(3,4-dimethoxyphenyl)-2-isopropyl valeronitrile of formula I is known since more than 20 years and the synthesis thereof is described in Belgian Pat. No. 615,816 corresponding to U.S. Pat. No. 3,261,859, to Dengel.

Verapamil chlorhydrate is used in medicine in view of its outsetting properties as the calcium intracellular penetration antagonist. This characteristic makes from it an interesting medicine for the treatment of angor pectoris when the crisis or attack is bound to a coronary spasm and when undesirable effects of beta-adrenolytic products such as propranolol, timolol, atenolol and pindolol, are to be feared for. Said substance is also useful in the treatment of hypertension or too high blood pressure and of troubles of the cardiac rhythm.

It is known from the skilled men that the pharmacological action of verapamil is proportional to its plasmatic concentration (Br. J. Clin. Pharmac. (1981), 12, 397–400) and that the optimum therapeutic zone is comprised between 100 ng/ml and 400 ng/ml of plasma.

The major disadvantage of a treatment based upon verapamil is due to its very short plasmatic half-life period (2 to 4 hours), which requires several daily administrations spaced of 6 hours only. Such near administration times render the treatment very annoying or even impossible to be carried out, particularly by night. Moreover, after each administration of a galenic form of verapamil with immediate release, i.e. generally four times per day, a succession of fast increasing and decreasing plasmatic ratios are established. The organism and namely the targed-organ, more particularly the heart, are alternatively subjected to overdoses and to underdoses of medicine.

In order to palliate these drawbacks, a first galenic form with sustained-release of verapamil, called "Isoptine Retard ®" and presented as a tablet constituted of an hydrophilic matrix, was put onto the market. Although said sustained-release galenic form allows to eliminate concentration peaks, the bioavailability of verapamil from this galenic form is extremely low, such as will be told hereinafter, so that said form does not permit to achieve practically the plasmatic therapeutic ratios and, consequently, renders difficult the obtention of a satisfying clinical effect.

SUMMARY OF THE INVENTION

The present invention relates to novel galenic forms of verapamil with sustained-release of said active substance, said novel galenic forms showing an excellent bioavailability, while avoiding the plasmatic concentration peaks, so that it is now possible not only to maintain the verapamil plasmatic concentrations in the actually effective range, but also to simplify dosage, since said novel forms do not necessitate more than one or two daily administrations of the medicine, depending on the patient's metabolism.

According to the present invention, said novel galenic forms with verapamil sustained-release are substantially characterized by the fact that they are constituted of microgranules containing a pharmacologically acceptable verapamil addition salt with an acid, such as verapamil chlorhydrate, as an active substance, associated to at least a wetting agent, said microgranules being coated with a microporous membrane constituted of at least a synthetic polymer associated to at least a pharmacologically acceptable adjuvant.

According to another feature of the present invention, the microporous membrane whereof the verapamil salt containing microgranules are coated is constituted of at least one synthetic polymer associated to at least one adjuvant selected from plastifying agents, pigments, fillers, wetting agents, lubrifying agents or lubricants, antistatic and antifoaming agents.

BRIEF DESCRIPTION OF THE INVENTION

The active substance containing microgranules are presented in form of spherules the diameter of which is comprised between 0.05 mm and 3 mm, preferably between 0.1 mm and 2 mm.

Among the wetting agents associated to the verapamil chlorhydrate into said microgranules, the following compounds may more particularly be examplified:
saccharose, mannitol, sorbitol;
lecithins;
polyvinylpyrrolidones;
$C_{12}$ to $C_{20}$ fatty acid esters of saccharose, commercialized under the name of sucroesters (Gattefosse, France) or under the name of crodesters (Croda, U.K.);
$C_{12}$–$C_{20}$ glycerides of saccharose or sucroglycerides glycerides;
xylose esters or xylites;
polyoxyethylenic glycerides;
esters of fatty acids and polyoxyethylene (Tefose of Gattefosse, France-Cremophors of BASF, RFA);
ethers of fatty alcohols and polyoxyethylene (Brijs, Renex and Eumulgines, Henkel, RFA);
sorbitan fatty acid esters (Spans, Atlas, U.S.A.);
sorbitan fatty acid polyoxyethylene esters (Tweens, Atlas, U.S.A.);
polyglycides-glycerides and polyglycides-alcohols esters (Gelucires, Gattefosse, France).

In addition to at least one of the abovenamed wetting agents, said microgranules may contain excipients or carriers, such as:
microcrystalline celluloses, such as Avicel products (FMC, U.S.A.);
methylcelluloses, ethylcelluloses (Ethocel or Aqua Coat), carboxymethylcelluloses, hydroxythylcelluloses (Natrosol, Hercules, U.S.A.), hydroxypropyl celluloses (Klucels, Hercules, U.S.A.);
starches.

Among the polymers constituting the microporous membrane, may be mentioned particularly polyacrylates and polymethacrylates of the Eudragit type, such as Eudragit E30D, L30D, RS, RL, S, L of Röhm Pharma (RFA), ethylcelluloses, such as Ethocels of DOW, U.S.A. and such as AquaCoat of FMC, U.S.A., polyvinyl chlorides, such as the Pevikons of Kemanord, Sweden and ethylene-vinyl acetate copolymers.

Said polymers may be associated into the microporous membrane to at least an adjuvant selected from the following:

plastifying agents, such as triacetine, dibutylphthalate, dibutylsebacate, citric acid esters, polyethyleneglycols, polypropyleneglycols and polyvinylpyrrolidone;

possibly coloured pigments, such as iron oxides and titanium oxide;

fillers, such as lactose and sucrose;

wetting agents, such as surfactive agents of the Span and Tween types, namely partial esters of fatty acids (lauric, palmitic, stearic and oleic acids) and anhydrides of hexitols derived from sorbitol possibly containing polyoxyethylenic chains, preferably surfactive agents of the Tween type, namely Tween 80, as well as polyethyleneglycols;

lubricants, such as magnesium stearate and talc;

antifoaming agents, such as silicone oil;

antistatic agents, such as colloidal aluminium oxide.

As other adjuvants which may possibly be used in combination with the microporous membrane forming polymers, these integrating agents such as starches and derivatives thereof may be used.

In addition to the polymer(s), said microporous membrane contains, preferably, talc and/or magnesium stearate as lubricant, polyvinylpyrrolidone as plastifying agent, titanium bioxide as pigment, Tween 80 as wetting agent, colloidal aluminium oxide as antistatic agent and silicone oil as antifoaming agent.

The weight of the microporous membrane may be 2 to 35%, preferably 5 to 22%, of the weight of said microgranules. These microgranules may contain verapamil chlorhydrate in an amount of 20 to 95% by weight, preferably 30 to 85% by weight.

The microporous membrane may contain 5 to 95% and, preferably, 30 to 90% of polymers or polymer mixture.

The invention relates also to a medicine containing verapamil as a sustained-release ingredient, said medicine being constituted of microgranules containing verapamil, preferably in the form of its chlorhydrate and at least a wetting agent, coated with at least one polymer-based microporous membrane, said coated microgranules being contained in capsules, little bags or dosage dispensers.

The present invention relates also to a process for obtaining novel forms of verapamil with sustained- and/or delayed-release in the gastro-intestinal tractus, said process comprising previously preparing microgranules and coating same with a microporous membrane.

Several known techniques may be used for obtaining microgranules containing verapamil chlorhydrate. A first technique consists in mixing verapamil chlorhydrate with the wetting agent(s) in a melted or finely divided form, or in solution, in the presence of a solvent, such as water or an hydroalcoholic mixture, so as to obtain an extrudable paste or plastic mass.

Said paste is thereafter extruded in an extruder and the extruded product is rendered spherical. Preferably, an extruder is used with a die having a diameter comprised between 0.1 mm and 3 mm, preferably between 0.5 mm and 2 mm. Several extruder types are usable, for example the extruder of ALEXANDERWERK (RFA) or the apparatus called X-truder of FUJI-PAUDAL (Japan). For obtaining microspheres or microgranules from the extruded product provided in the form of little cylinders, an apparatus called "spheronizer" of the CALEVA (Great-Britain) or MARUMERIZER (FUJIU-PAUDAL Japan) type is used.

Another technique for obtaining microgranules consists in spraying and/or dusting cores obtained through agglomeration of verapamil chlorhydrate contingently mixed to at least a wetting agent, with an organic or aqueous dispersion or solution of at least one wetting agent, for example in a known pilling turbine or in a granulating apparatus, such as the CF granulator system of FREUND INDUSTRIAL CO. (Japan), or in a known planet granulator.

The obtained microgranules are dried by any means, for example in an oven or by means of a gas in a fluidized bed.

Finally, said microgranules are calibrated to the necessary diameter by passage through appropriate screens.

A pasty or plastic mixture, appropriate to be granulated by means of anyone of the above described techniques, may contain the following weight proportions of verapamil chlorhydrate, wetting agents and carriers or excipients:

20 to 90% verapamil chlorhydrate;
15 to 30% sucroesters WE 15 (wetting agent);
8 to 15% Avicel PH 101 (microcrystalline cellulose of FMC, U.S.A.);
2 to 25% Avicel CL 611 (microcrystalline cellulose of FMC, U.S.A.);
2 to 35% sucrose (wetting agent);
2 to 10% Methocel E 5 (hydroxypropylmethylcellulose of DOW, U.S.A.);
1 to 15% polyvinylpyrrolidone and
5 to 30% distilled water.

Said microporous membrane may be applied onto said microgranules by pulverizing an hydroalcoholic or aqueous dispersion of at least one of the above-named polymers and at least one of the above-mentioned adjuvants onto said microgranules. This pulverization may be carried out by spray-gunning or by pulverizing the above-named dispersion into a turbine or a fluidized bed.

According an illustrative embodiment of the present invention, said microporous membrane may be obtained, starting from an aqueous dispersion which contains by weight:

10 to 45% Eudragit E30D (polymer);
5 to 70% Eudragit L30D (polymer);
1 to 25% talc (lubricant);
1 to 15% polyvinylpyrrolidone (plastifying agent);
0.05 to 4% colloidal aluminium oxide (antifoaming agent), or
0.01 to 2% silicone oil (antifoaming agent);
10 to 70% water (carrier).

EXAMPLES

The whole of the features and advantages of the invention will be better understood by the skilled men, referring to the following disclosure of particular non-limitative embodiments given by way of examples of the novel verapamil galenic form, its manufacturing process and its therapeutic applications, especially in relation with pharmacocinetic controls using said novel galenic form.

Examples of preparation of the new galenic form

EXAMPLE 1 a. Manufacture of microgranules

The following ingredients were used:

| | |
|---|---|
| Verapamil HCl | 325 g |
| Sucrose | 125 g |
| Avicel PH 101 | 25 g |
| Methocel E5 | 20 g |
| Polyvinylpyrrolidone K30 | 5 g |
| | 500 g |

After introducing the powders into a planet mixer and granulating same through the addition of 75 g of distilled water, the obtained plastic mass was extruded through the 1 mm-diameter holes of a cylindrical die of an extruder (Alexanderwerk). The obtained little cylinders were thereafter made spherical by spheronization into a Marumerizer type apparatus. After drying during 24 h into a ventilated oven brought to 50° C. the fraction of microgranules the diameter of which is comprised between 0.7 mm and 1.4 mm was recovered by screening through appropriate screens. 437 g of microgranules (yield: 87%) were so obtained.

b. Coating of microgranules

Onto 400 g of microgranules, the size of which is comprised between 0.7 and 1.4 mm, was gun-sprayed into a Strea I type Aeromatic fluidized bed apparatus, 176 g of the following dispersion:

| | |
|---|---|
| magnesium stearate | 7.50 g |
| titanium bioxide | 6.25 g |
| polyvinylpyrrolidone | 6.25 g |
| Tween 20 | 0.20 g |
| verapamil chlorhydrate | 6.25 g |
| water | 145.25 g |
| Eudragit E30D | 328.30 g |
| | 500.00 g |

Duration of the gun-spraying: 45 minutes
Drying into the oven at 50° C. during 24 hours.

It must be emphasized that the verapamil chlorhydrate contained in the membrane applied onto the microgranules is intended to be fastly released after the administration of the pharmaceutical composition.

c. Pharmaceutical compositions

After screening and control of the content of the microgranules in verapamil chlorhydrate and after having adjusted said content to the desired value through addition of neutral microgranules, such as sucrose microgranules, the mixture was introduced into hard gelatine capsules in order to obtain the desired verapamil unit dosage.

d. Measures of the verapamil release-speed out of the microgranules

In order to ascertain the quality of the verapamil sustained-release preparation, a method was used, described in "The United States Pharmacopoeia (USP) XXI", edition 1985, p. 1243–1244, under the title Dissolution Apparatus II, the dissolving medium being constituted of a buffer of pH=5.8. 215.5 mg of microgranules of example 1 per flask were used.

The following results have been obtained during said dissolution.

| Time | % of verapamil HCl dissolved ± SD (standard deviation) |
|---|---|
| After 1 h | 1.6 ± 0.2 |
| After 4 h | 27.0 ± 0.3 |
| After 8 h | 84.2 ± 0.5 |

The novel galenic form according to the invention hereabove described was subjected to an extensive pharmacocinetic study, compared to an immediate release form (Isoptine ®) and to a delay-form actually available in the commerce (Isoptine Retard ®).

Five voluntary subjects have received successively and in a random order each of the three forms at a 2 week's interval, at equivalent doses (360 mg of verapamil). The determination of the cinetic of the verapamil plasmatic concentrations has been carried out by means of 14 to 16 sample takings and provided the curves of the joined FIG. 1.

Figure 1:
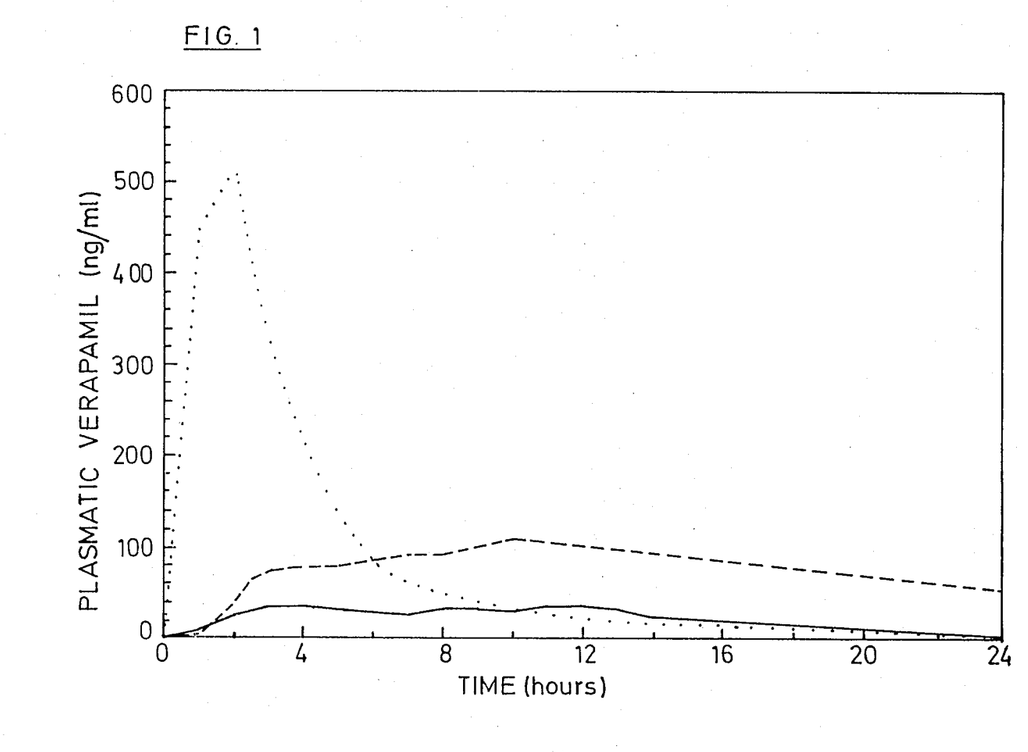
FIGS. 1–5 provide the verapamil plasmatic concentrations as a function of time.

On said FIG. 1, the dotted curve relates to the normal Isoptine, the dashed curve relates to the galenic form according to example 1 and the continuous curve relates to Delay-Isoptine.

Five healthy voluntary subjects have also received the novel galenic form of verapamil according to example 1 during one week, in an amount of one dosage of 360 g of verapamil chlorhydrate every 24 hours. The evaluation curve of the plasmatic ratios (given in ng/ml) was obtained by means of 17 blood takings (see FIG. 2).

At the end of said study, the conclusions were as follows:

1. Administration in unit dosages (FIG. 1)

1.1 Bioavailability

According to the values of the surfaces under the curves, plasmatic concentrations on ordinates time from 0 to 24 h on abscissa (non infinite-extrapolated values), the bioavailability of the galenic form according to example 1 appears to be equivalent (88.5%) to that of the immediate release product, whereas the bioavailability of the Delay-Isoptine product is definitely lower, as said bioavailability achieves only 26% of that of the rapid release product.

1.2 Course of the plasmatic curves

Both sustained release forms give practically parallel curves the course whereof is characteristic of such a galenic preparation type.

Figure 2:
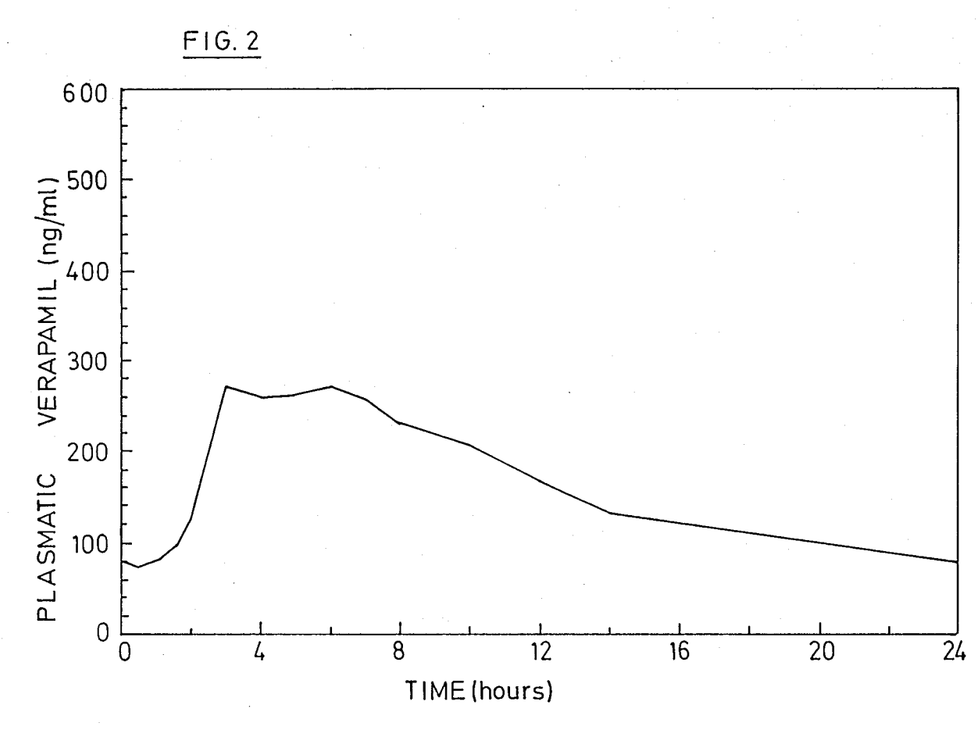

2. Administration of repeated dosages (FIG. 2)

The mean curve of the plasmatic ratios, given in ng/ml, obtained after the eighth daily oral dose of 360 mg of verapamil chlorhydrate in the galenic form of example 1, lies, practically during 24 hours (i.e. in the interval comprised between successive doses), within an optimum therapeutic range.

EXAMPLE 2 a. Manufacture of microgranules

The following amounts of products, given in grams, were used:

| | |
|---|---|
| verapamil HCl | 480 |
| sucroester WE 15 | 60 |
| Avicel | 60 |
| water for granulation | 165 |

The preparation process was the same as in example 1, with the provision that a XTRUDER extruder (Fuji-Paudal) was used. 524 g of microgranules were obtained (yield: 87.33%).

b. Coating of microgranules

The same process as in example 1 was carried out. Onto 500 g of microgranules were sprayed 305 g of the following aqueous dispersion (amounts given un g):

| | |
|---|---|
| talc | 50.00 |
| polyvinylpyrrolidone | 7.50 |
| Tween 20 | 0.20 |
| distilled water | 302.30 |
| Eudragit E30D | 452.50 |
| Eudragit L30D | 187.50 |
| | 1000.00 | c. Pharmaceutical form

The pharmaceutical form has been obtained by working as described in example 1.

d. Measure of the verapamil release of said micro granules

Using the same method and analysis equipment as described in example 1, the following results were obtained:

| Time | % verapamil HCl dissolved ± SD |
|---|---|
| After 1 h | 1.5 ± 0.1 |
| After 4 h | 29.8 ± 1.0 |
| After 8 h | 74.2 ± 0.8 |

The novel galenic form of example 2 according to the invention was subjected to an extensive pharmacocinetic study in comparison with the immediate release form (Isoptine ®) and with the delay form presently available on the market (Isoptine Retard ®).

Five voluntary subjects received successively each of the three forms at an interval of 2 weeks at equivalent dosages (360 mg of verapamil) and in a random order.

Figure 3:
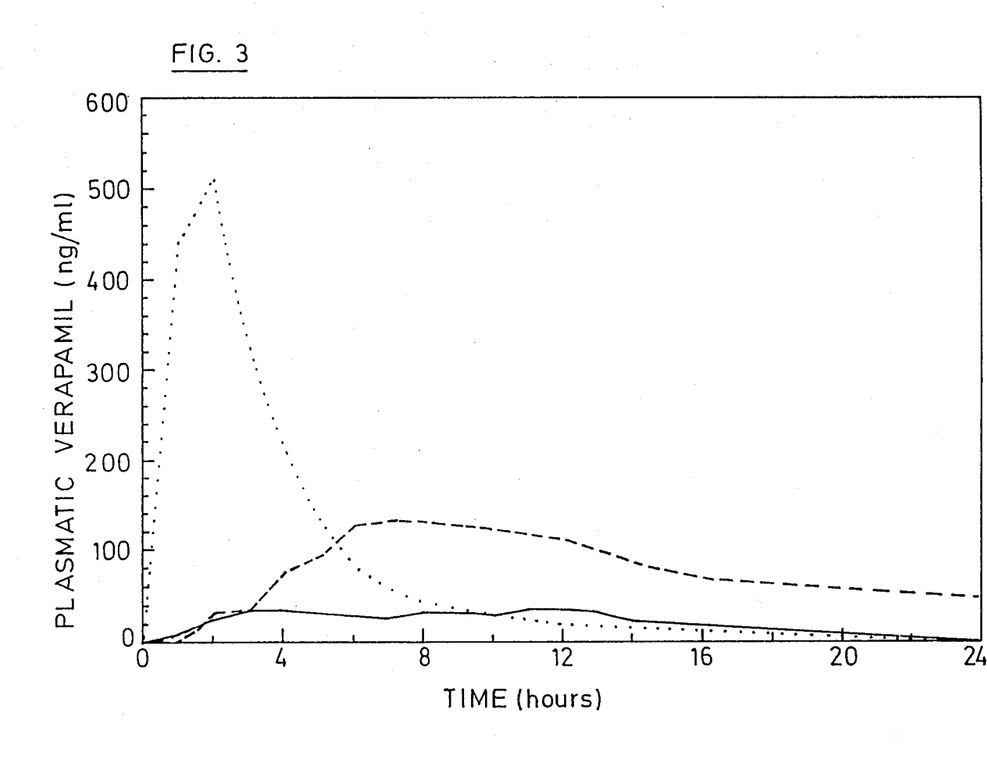

The plasmatic ratios (given in ng/ml) for measuring the verapamil blood concentration evolution have been established by means of 14 to 16 blood takings (see joined FIG. 3).

Figure 4:
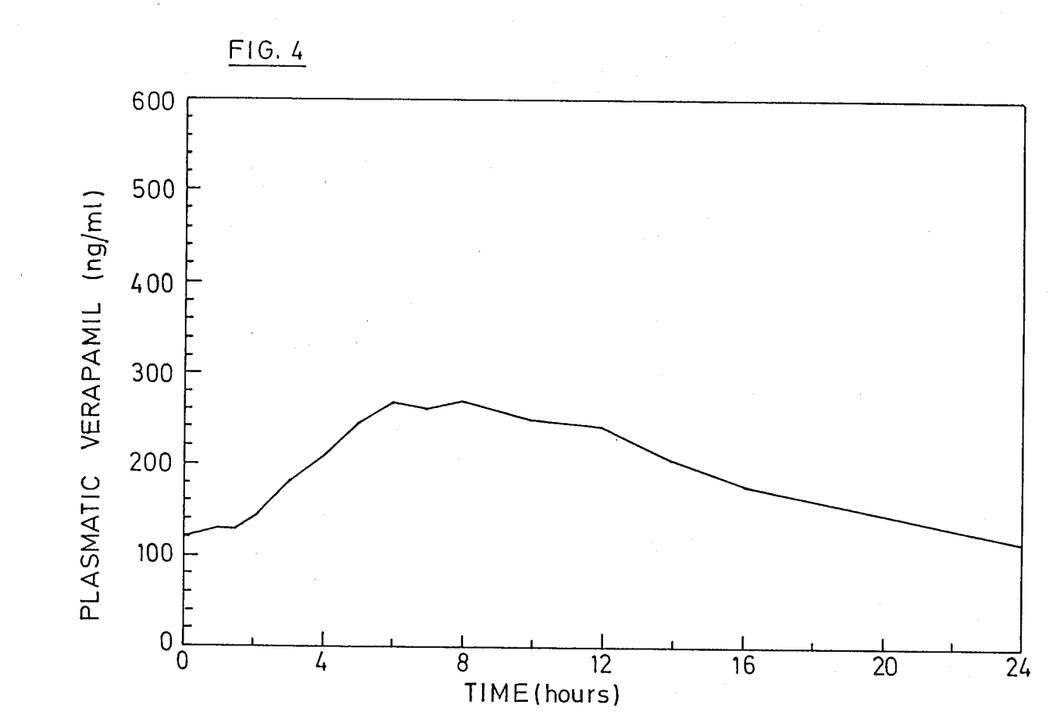

The verapamil plasmatic ratio evolution was also measured after the eighth oral dose repeated in five healthy subjects at the rate of one 360 mg dose per 24 h, calculated as verapamil chlorhydrate in the galenic form of example 2 (FIG. 4).

At the end of said study, the conclusion is that: with regard to the compared bioavailabilities and the plasmatic curve courses, the conclusions given at the end of the study of example 1 are valuable for this example 2, both in the case of sole dosages and in the case of repeated dosages.

EXAMPLE 3

The study of the influence of a wetting agent in the composition of said microgranules could be carried out after having prepared a galenic form using the method and the equipment described in example 2, but substituting for the wetting agent of example 2, namely sucroester WE 15, lactose which is an inert powder without wetting properties, the microporous membrane being quantitatively and qualitatively identical to the one of example 2.

The so obtained galenic form was subjected to an extensive pharmacocinetic study compared with the form of example 2.

Figure 5:
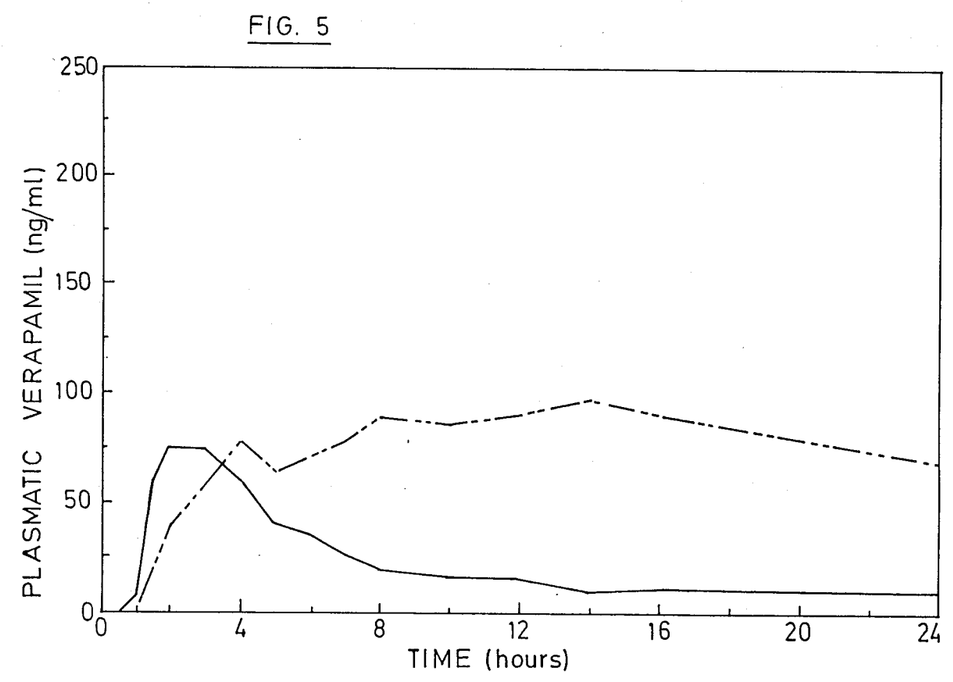

For this purpose, five healthy voluntaries received successively each of both forms at an interval of 2 weeks at equivalent dosages (360 mg of verapamil chlorhydrate) and in a random order. The plasmatic ratios (given in ng/ml) for the measure of the verapamil blood concentration evolution were established by means of 14 blood takings (see joined FIG. 5).

At the end of said study, the conclusions are that:

1. The bioavailability of the form without wetting agent achieves only 29.6% of the bioavailability of the form with a wetting agent of example 2.
2. Although the galenic form without wetting agent has a more rapid absorption than the form of example 2 during the two first hours, the plasmatic ratios obtained with said form without wetting agent are not sustained at all, are extremely low and insufficient.

On a clinical point of view, the characteristics of sustained or continuous and slow release of verapamil from the microgranules of the novel galenic forms according to the invention have given raise to the disclosure of the following important advantages:

Better accession of the patient to its treatment, for the reason that the number of daily medicine doses is reduced. In general, the novel galenic form requires only solely one daily administration, whereas an equivalent treatment by means of immediate release preparations comprises four daily doses, i.e. a dose every 6 hours.

Increase of the therapeutic efficiency, on the first hand thanks to the maintaining of efficient plasmatic concentrations during the whole space of time separating two successive doses of medicine and, on the other hand, owing to the suppression of the succession of peaks (temporarily too high plasmatic concentrations) and valleys (too low concentrations).

Reduced risks and increased ease in the adjustment of the individual posology, thanks to an important reduction of the plasmatic ratio variations from one patient to the other.

Consequently, it may be positively stated the novel galenic forms according to the present invention provide a useful novel medicine for treating cardiac rhythm disorders, hypertension or high blood pressure, angor pectoris or all other medical use of verapamil through oral administration.

It must be emphasized that the skilled men will be able to discover other advantages and variations of the invention, more particularly relating to the process for obtaining said microgranules and said membrane serving to control the release of the active substance, without departing from the present invention as defined in the following claims.

We claim:

1. Galenic form of verapamil chlorhydrate with sustained release of said compounds, comprising a microgranules containing verapamil chlorhydrate and at least one wetting agent selected from the group consisting of sucrose, polyvinylpyrrolidone, $C_{12}$ to $C_{20}$ fatty acid esters of sucrose and xylose, sucrose glycerides, fatty acid esters of polyoxyethylene, fatty alcohol ethers of polyoxyethylene, sorbitan esters, polyoxyethylene sorbitan esters, polyglycides-glycerides, polyglycides-alcohols esters and lecithins, said microgranules being coated with a microporous membrane constituted of at least a synthetic polymerisate of acrylic acid ethylesters and methacrylic acid methylesters and at least a pharmacologically acceptable adjuvant selected from the group consisting of plastifying agents, pigments, fillers, wetting agents, lubricants and anti-foaming agents.

2. Galenic form of verapamil chlorhydrate according to claim 1, wherein said active substance, containing microgranules are present in the form of spherules, the diameter of which is comprised between 0.1 mm and 2 mm.

3. Galenic form of verapamil chlorhydrate according to claim 1, wherein said microporous membrane weight makes from 5 to 22% of the weight of the microgranules coated by same.

4. Galenic form of verapamil chlorhydrate according to claim 1, wherein said active substance containing microgranules are present in the form of spherules the diameter of which is comprised between 0.05 mm and 3 mm.

5. Medicine containing verapamil chlorhydrate to be administered through oral way, Comprising a galenic form according to claim 1 contained in a capsule, a bag or a dosage dispenser.

6. Galenic form of verapamil chlorhydrate according to claim 1, wherein the pharmacologically acceptable adjuvant of said microporous membrane coating said microgranules is
- a plastifying agent selected from the group consisting of triacetine, dibutylphthalate, dibutylsebacate, citric acid esters, polyethyleneglycols, polypropyleneglycols and polyvinylpyrrolidone; or
- a contingently colored pigment selected from the group consisting of iron oxides and titanium oxido; or
- a filler selected from the group consisting of lactose and sucrose; or
- a wetting agent selected from the group consisting of fatty acid partial esters anhydrides of hexitols derivated from sorbitol contingently containing polyoxyethylenic chains and the polyethylene glycols; or
- a lubricant selected from the group consisting of magnesium stearate and talc; or
- a silicone oil as antifoaming agent or; a colloidal aluminum oxide as antistatic agent.

7. Galenic form of verapamil chlorhydrate according to claim 6, wherein said microporous membrane contains, in addition to the polymer(s), talc and/or magnesium stearate, as a lubricant, polyvinylpyrrolidone as a plastifying agent, titanium dioxide as a pigment, colloidal aluminum oxide as an antistatic agent and silicone oil as an antifoaming agent.

8. Galenic form of verapamil chlorhydrate according to claim 1, wherein said microgranules contain, by weight, 20 to 90% of verapamil chlorhydrate, as well as 5 to 30% of $C_{12}$ to $C_{20}$ fatty acid esters of saccharose, 4 to 50% of microcrystalline celluloses, 0 to 35% sucrose 0 to 10% hydroxy-propylmethylcellulose and 0 to 15% polyvinylpyrrolidone, as wetting agents and carriers or excipients.

9. Galenic form of verapamil chlorhydrate according to claim 8, wherein said microgranules contain, by weight, about 65% verapamil chlorhydrate, as well as 25% sucrose, 5% of microcrystalline celluloses, 4% hydroxypropylmethylcellulose and 1% polyvinylpyrrolidone, as wetting agents and carriers or excipients.

10. Galenic form of verapamil chlorhydrate according to claim 8, wherein said microgranules contain, by weight, about 80% verapamil chlorhydrate as well as 10% of $C_{12}$ to $C_{20}$ fatty acid esters of saccharose as wetting agent and 10% microcrystalline cellulose as carrier or excipient.

11. Galenic form of verapamil chlorhydrate according to claim 6, wherein said microporous membrane coating said microgranules contains, by weight, 5 to 95% of at least said polymerisate, 1 to 25% talc or magnesium stearate, 0 to 4% colloidal aluminum oxide, 0 to 15% polyvinylpyrrolidone, 0 to 2% silicone oil and 0 to 0.5% of sorbitan fatty acid polyoxyethylene ester as wetting agent.

12. Galenic form of verapamil chlorhydrate according to claim 6, wherein said microporous membrane coating said microgranules comprises, by weight, 70 to 80% of at least said polymerisate, 6% magnesium stearate, 4 to 6% titanium dioxide, 4 to 6% polyvinylpyrrolidone and 0.1% sorbitan fatty acid polyoxyethylene esters.

13. Galenic form of verapamil chlorhydrate according to claim 6, wherein said microporous membrane contains by weight, 60 to 80% of at least said polymerisate, 10 to 25% talc, 1 to 5% polyvinylpyrrolidone and 0.05% sorbitan fatty acid polyoxyethylene ester.

14. Galenic form of verapamil chlorhydrate according to claim 1, wherein said microporous membrane itself contains also verapamil chlorhydrate.

15. Galenic form of verapamil chlorhydrateU according to claim 1, wherein said microporous membrane weight makes from 2 to 35% of the weight of the microgranules coated by same.

16. Medicine according to claim 5, wherein said medicine is in the form of unit dosages containing from 20 to 400 mg verapamil chlorhydrate.

17. Medicine according to claim 5 wherein said medicine is in the form of unit dosage containing from 50 to 360 mg verapamil chlorhydrate.

* * * * *